United States Patent [19]
Malmin

[11] 3,974,831
[45] Aug. 17, 1976

[54] CARTRIDGE AND SEALING MEANS THEREFOR

[76] Inventor: Oscar Malmin, 127 E. Wayne Ave., Akron, Ohio 44301

[22] Filed: Sept. 26, 1974

[21] Appl. No.: 509,424

[52] U.S. Cl. .......................... 128/218 D; 128/272; 32/40 R
[51] Int. Cl.² .......................................... A61M 5/00
[58] Field of Search ............ 128/272, 218 D, 218 P, 128/218 DA, 218 M, 219, 218 NV; 32/40, 57

[56] References Cited
UNITED STATES PATENTS

| | | | |
|---|---|---|---|
| 2,132,763 | 10/1938 | Smith | 128/218 D |
| 2,268,994 | 1/1942 | Smith | 128/218 D |
| 2,453,590 | 11/1948 | Poux | 128/218 D |
| 2,545,017 | 3/1951 | Billingsley | 128/218 D |
| 2,706,984 | 4/1955 | Lipari | 128/218 P |
| 2,895,773 | 7/1959 | McConnaughey | 128/219 X |
| 3,084,688 | 4/1963 | McConnaughey | 128/218 NV |
| 3,255,752 | 6/1966 | Dick | 128/218 M |
| 3,742,948 | 7/1973 | Post et al. | 128/218 P |
| 3,807,048 | 4/1974 | Malmin | 32/40 R |
| 3,810,469 | 5/1974 | Hurschman | 128/218 M |
| 3,850,174 | 11/1974 | Ayres | 128/272 |

Primary Examiner—John D. Yasko

[57] ABSTRACT

An improved cartridge for use in hypodermic syringes is disclosed in which the hollow tubular cartridge body has a first end which has a resilient seal thereon and which engages both the end of the cartridge and a portion of the periphery thereof adjacent the end. The first seal member is also capable of engaging the internal nozzle of the syringe, if one exists, as well as engaging the inner surface of the barrel of the syringe. The opposed end of the cartridge body, which is normally contacted by a plunger to eject the contents, has a second seal member or plug, at least a portion of which is partially received internally of the cartridge and has annular ribs which perform as O-rings and contact the inner surface thereof for sealing purposes. A lip fits over the second end of the cartridge body to achieve a three-way seal at that point and also seals against the inner surface of the barrel of the syringe per se. This second seal member is deformable so that upon actuation of the plunger, the second seal will deform inside the cartridge body to resist back pressure and thereby prevent leakage.

4 Claims, 7 Drawing Figures

U.S. Patent   Aug. 17, 1976   3,974,831
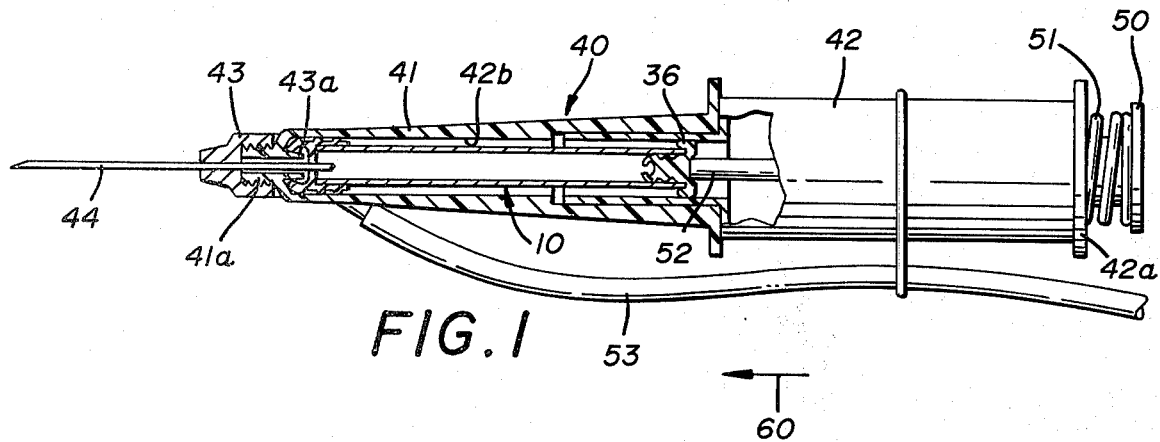
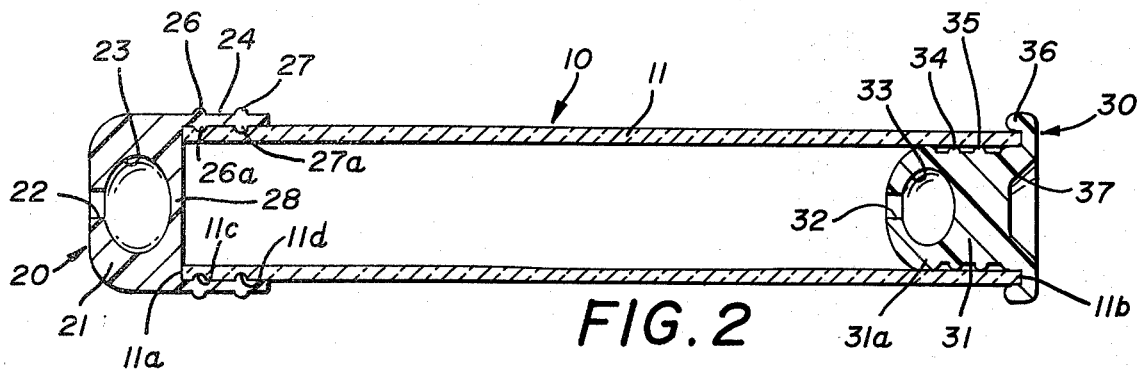
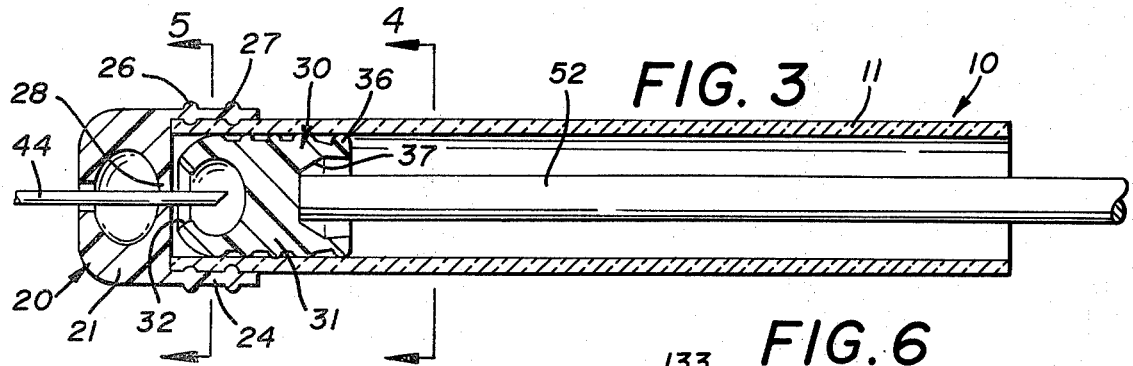
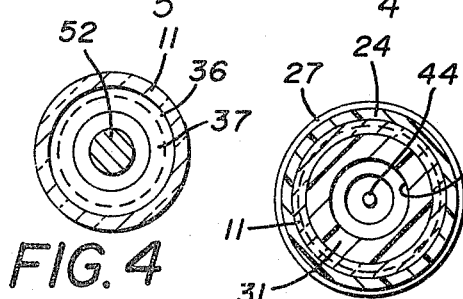
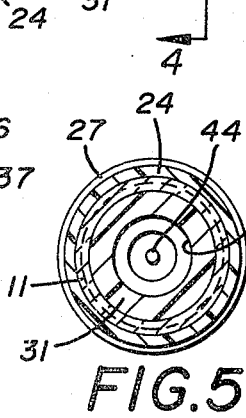
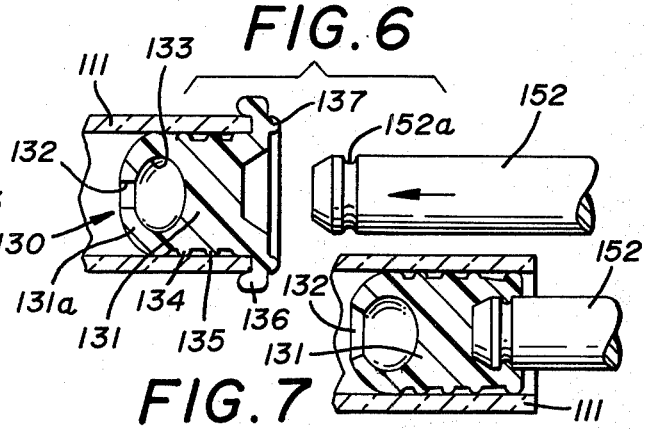

CARTRIDGE AND SEALING MEANS THEREFOR

BACKGROUND OF THE INVENTION

This invention relates, in general, to disposable cartridges such as are commonly used for local anesthetics and are commonly used in syringes having plungers at one end and double-ended needles at the other so that the plunger forces the cartridge forward onto the needle, thereby perforating its seal and permitting its contents to be expelled to the other end of the needle. In particular, the invention relates to an improved seal at both ends of the cartridge so as to permit sterilization of the same while at the same time preventing any leakage or contamination of the contents thereof.

DESCRIPTION OF THE PRIOR ART

The following patent prior art is known to Applicant:

| | |
|---|---|
| Reznek | U.S. Pat. No. 2,895,473 |
| McConnaughey | U.S. Pat. No. 2,895,773 |
| Jalar et al | U.S. Pat. No. 2,904,044 |
| Camber | U.S. Pat. No. 2,966,910 |
| Hart | U.S. Pat. No. 2,986,141 |
| McConnaughey | U.S. Pat. No. 3,084,688 |
| Knox | U.S. Pat. No. 3,561,596 |
| Cohen | U.S. Pat. No. 3,577,980 |
| Hurschman | U.S. Pat. No. 3,810,469 |

In addition to the aforementioned patent prior art, Applicant is also aware of the conventional cartridge which has an elongated glass or plastic body having a constricted neck formed adjacent one end thereof, with a thin rubber membrane being stretched over the top or end of the cartridge and a compressible or crimpable aluminum collar being secured thereabout and engaging the constricted neck thereof.

The opposed end of the conventional cartridge has a plug of one of two general forms. The first of these is a solid plug, and the second is a deformable plug which is intended specifically to create a "kick-back" action which acts to create an aspirating or negative pressure function. These plugs also normally possess one or more annular rings to act as O-ring seals on the internal surface of the cartridge body.

Cartridges of this type have been in use for years, but there are certain disadvantages thereto.

First, it is necessary to mold the cartridge with the constriction or reduced diameter "neck" therein which is an added expense and step in manufacture of the same.

Second, cartridges of this type cannot normally be placed in a cold sterilizing solution because the seals on either end are susceptible to leaking, permitting the sterilizing solution to contaminate the injectable agent contained within the cartridge.

Third, the aluminum cap or collar is susceptible to being attacked and corroded by many chemical agents which can cause a failure of the seal and leakage.

Fourth, the rubber membrane or diaphragm which is stretched across the end of the cartridge does not frictionally seize the perforating diameter of the needle as securely as a passive membrane might. This is so because the passive membrane will have a higher degree of elasticity than the conventional one.

Fifth, the seal on the opposed end of the cartridge is capable of being compressed in an eccentric manner when the plunger is off-center to any degree, thereby causing the rubber to distort with a consequent binding action between the plug or seal and the surface of the cartridge. This makes the injection action both difficult for the operator and jerky and conceivably painful and uncomfortable to the recipient.

Sixth, the rubber plug in this end of the cartridge usually requires sealing with wax to avoid leakage due to the fact that variances and tolerances during manufacture occur and the fit of the plug within the cartridge is thereby effected.

Seventh, plugs of the conventional variety do not have any method of precisely fixing their degree of penetration into the cartridge. Stated otherwise, the plug may be found to vary in its position in relation to the end of the cartridge.

Eighth, the cartridge also has no means for fixing its position relative to the barrel of the syringe. Thus it can become off-center instead of concentric as desired.

SUMMARY OF THE INVENTION

It is believed that all of the foregoing disadvantages can be obviated by the present invention.

For example, it has been found that by providing the cartridge on its end adjacent the needle with a seal of a single, unitary, molded piece of resilient material, such as rubber or some resilient form of plastic, having a main body portion which overlies the end of the cartridge and a projecting annular portion which engages the sides thereof, an improved seal can be achieved. With this type of seal it is not necessary to have a molded "neck" on the cartridge per se since the annular portion, which preferably has circumferential ribs thereon, will securely engage this surface for sealing purposes.

It has also been found that if the main body portion has an outboard projecting end with an aperture therein opening into an enlarged chamber, the needle will readily pass through the aperture and the chamber and, upon movement of the cartridge toward the needle, the projections will engage the internal nozzle of the syringe, thereby again assuring a secure seal. In this regard the syringe illustrated herein has such a nozzle, but it is believed that the present invention has equal utility with a syringe lacking this feature.

Furthermore, it has been discovered that by having a reduced thickness portion of the seal body overlying the end of the cartridge body, that when the needle perforates, this material, being inherently resilient, will frictionally engage the periphery of the needle thereby insuring a seal at that point.

It has also been discovered with regard to the plug or sealing member at the opposed end of the cartridge that the operation of the same can be greatly improved by providing a resilient, deformable plug, the main body portion of which is received internally of the cartridge.

This plug has lips on its rear end, and these, in the initial configuration, fit over the end of the cartridge body thereby providing a very secure seal both with regard to the interior of the cartridge and between the cartridge and the barrel of the syringe.

The cartridge body also has circumferential rings about it and a projection which has a slight opening or bore in its outboard end opening into an enlarged chamber. By virtue of this construction, upon actuation of the plunger, the second seal or plug will roll inwardly and deform and be forced down along the body of the cartridge, thereby preventing any back pressure leakage such as is often found in conventional cartridges.

Additionally, a centering area is provided on the outboard end of the second seal to guide the plunger and assure coaxial movement.

Accordingly, production of an improved cartridge and sealing means therefor of the general character above-described becomes the principal object of this invention, with other objects thereof becoming more apparent upon a reading of the following brief specification, considered and interpreted in view of the accompanying drawings.

OF THE DRAWINGS

FIG. 1 is an elevational view partially broken away in section showing the cartridge in place within the syringe.

FIG. 2 is an elevational view in section broken away to show the cartridge per se in its inoperative condition.

FIG. 3 is a view similar to FIG. 2 showing the plunger depressed and the needle engaging the first sealing member.

FIG. 4 is a sectional view taken on the lines 4—4 of FIG. 3.

FIG. 5 is a sectional view taken on the lines 5—5 of FIG. 3.

FIG. 6 is a partial sectional view similar to FIG. 2 showing a modified form of the invention.

FIG. 7 is a partial sectional view similar to FIG. 3 showing the modified form of the invention with the plunger depressed.

BRIEF DESCRIPTION OF THE PREFERRED EMBODIMENTS

Referring first to FIGS. 1 and 2, it will first be noted that the cartridge 10 basically consists of an elongate hollow, cylindrical body portion 11, a first seal member 20, and a second seal member 30.

To place the cartridge in its environment, reference is made to FIG. 1 wherein the syringe 40 is shown as having an elongate barrel 41 and a connecting housing 42. Received within the housing 42 is a spring-loaded plunger 50 which has a plunger rod 52 projecting inwardly therefrom. The plunger is normally urged to the outboard position by the spring 51 acting on the head 42a of the housing 42.

On the opposed end of the body 41, means are provided for receiving a needle 44 which is held in place thereon by a threaded connection between the needle housing 43 and the outboard end 41a of housing 41. A vacuum tube 53 is also provided for aspirating purposes. In the particular syringe illustrated in FIG. 1, the syringe has an internal nozzle 43a which may be engaged by first seal member 20, but it should be understood that the cartridge of this invention could also be used with syringes of different design.

Turning next then to FIG. 2 for a detailed description of the cartridge per se, it will be noted that the cartridge 11 has a forward end 11a. The cartridge as shown in FIG. 2 is an elongate cylindrical member of glass or similar material and, in the form of the invention shown in FIG. 2, has circumferential grooves 11c and 11d about its forward end. It should be understood, however, that this is only one version of the invention and that it is believed that the first sealing member, which will be described below, would work also with a cartridge body having a smooth uninterrupted outer surface.

The first seal member 20 has a main body portion 21 which at its outboard end has a through bore 22 for reception of needle 44 and opening into an enlarged opening 23. The body being of resilient, deformable material such as rubber, for example, it can be utilized with a syringe such as shown in FIG. 1 which has an internal nozzle 43a. If this type of syringe is employed, once the cartridge is seated, the walls of the bore 22 will be deformed by the nozzle 43a and will firmly grasp the same.

The main body portion 21 has a reduced thickness portion 28 which covers the end of the cartridge body 11. This area, in contrast to the membrane type covering of the conventional prior art, has a substantial thickness to it so that when the needle 44 perforates it, as shown in FIG. 3, it will securely grasp by friction the periphery of the needle, thereby insuring a seal therebetween.

The opposed end of the main body portion 21 has an annular projection 24, with this projection being of sufficient length to engage at least a portion of the outer surface of the cartridge body 11. In the form of the invention shown in FIG. 2, annular ring-like ribs 26 and 27 and 26a,27a are provided on both the outer and inner surfaces of the annular projection 24. In this form of the invention, as noted above, the cartridge body has annular grooves 11c and 11d adjacent its end, and the inner ribs 26a and 27a would engage these grooves. However, as also noted above, these grooves may not be absolutely essential and could be eliminated so that the cartridge would have a smooth outer surface; and if they were, it would be possible to eliminate the inner ribs 26a and 27a of the seal. Such a construction would however impair, to a certain degree, the sealing effect obtained by the preferred form of the invention. Additionally, if desired, to maintain the body thickness of the cartridge, the same could be formed with ring-like ribs on its outer surface and the seal with cooperating grooves on its inner surface to replace ribs 26a,27a. An alternating ring and groove arrangement or an arrangement with interrupted rings and grooves are also possible, but here again, in addition to presenting manufacturing problems, the locking and sealing capabilities of the preferred form of the invention would, to some extent, be diminished.

In any case the outer ribs 26 and 27 will contact the inner surface 42b of the barrel 41 of the syringe itself, thereby securely seating and concentrically locating the cartridge within the barrel 41. This feature also makes it possible to use the syringe for aspirating purposes through tube 53 by creating a sealed chamber adjacent the needle. A syringe capable of aspirating and injecting, illustrating the desirability of this feature, may be seen in Malmin U.S. Pat. No. 3,807,048.

Referring still then to FIG. 2 for a detailed description of the second seal or plug member 30, it will be noted that this also has a main body portion 31 which has circumferential ribs 34,35 therearound. The main body portion 31 is received within the cartridge body 11, and these ribs 34 and 35 engage the inner surface of the body 11. In this fashion they will serve as O-rings when the plunger is activated, as will be described.

The inboard end of body 31 terminates in an enlarged portion 31a which has a bore 32 therethrough opening into an enlarged chamber 33. This configuration permits an expansion of the plug 30 when the plunger is depressed, thereby insuring a tight seal in several places along the interior of the body.

The opposite end of the body 31 of second member 30 has a flange 36 which fits over the end 11b of the cartridge body 11 and thereby engages the same in three separate places. Provision of this flange also controls the depth of entry of body 31 into the cartridge thereby insuring uniformity. Furthermore, as will be seen from FIG. 1, this flange 36 also, at least initially, engages the inner surface 42b of the syringe barrel 41 itself, thereby serving to accurately seat the cartridge within the barrel. When the plunger rod 52 is activated, as shown in FIG. 3, the flange will curl up over the end 11b, and the entire seal 30 will pass down the length of the cartridge body, with the projections serving as O-rings to achieve a secure seal against any back pressure.

It also will be noted that the outboard end of the seal 30 has a beveled opening 37 therein. This will serve to guide the plunger rod 52 into a coaxial position with regard to the longitudinal axis of the cartridge. It is safe to assume that there is some "play" in the rod, and it is advantageous to seat it as accurately as possible with that axis so as to avoid any distortion and binding as the seal 30 is forced down the length of the cartridge body 11.

Accordingly, in operation of the device it is assumed that the cartridge 10 will be inserted within the barrel 41 of the syringe 40, with the plunger, etc., being in the position shown in FIG. 1 of the drawings. Assuming the needle 44 to have already been in place when the cartridge was inserted, the needle 44 would have passed through opening 22 in the first seal member and penetrated the reduced thickness body portion 28 as clearly shown in FIGS. 1 and 3. Upon actuation of the plunger in the direction of the arrow 60, the plunger rod 52 will contact the second seal 30 and drive it along the length of the cartridge simultaneously expelling the contents thereof through the needle 44.

Referring next then to FIG. 6, a modified form of the invention is shown with regard to the second seal member. In this regard the second seal 130 is constructed substantially similarly to the seal shown in FIG. 2 with one exception. Specifically the seal has a main body portion 131, a projecting end 131a with an opening 132 therein, and this opening leading to an expanded opening 133. The circumferential rings 134 and 135 are also provided, as is the lip 136.

In this form of the invention, however, an additional annular ring 137 is provided on flange 136, as will be shown in FIG. 7. Once the plunger rod 152, which has been modified to have an annular ring 137 adjacent its end, is depressed, the flange 136 will roll inwardly so that the annular rib 137 will engage the circumferential groove 152a. In this fashion still an additional seal is achieved.

Accordingly, it has been shown how a relatively simple, yet unique, improved seal can be provided for both ends of a cartridge for use in a hypodermic syringe. Such a seal not only permits sterilization without the fear of leakage or contamination, but greatly enhances the performance qualities and characteristics of the cartridge when in use within the syringe.

It should also be noted that by virtue of the ribs 26 and 27 on the first seal member and the rib 36 on the second seal member, the cartridge is effectively sealed at both ends within the barrel 41 of the syringe. This feature is important because cartridges of this nature have the capability of shattering or splitting under the hydraulic pressures involved in injection. In the event this happens, it is possible that particles of the material could be driven into the patient's tissue, and furthermore the local anesthetic solution could be "dumped" into the mouth in an unregulated manner with potentially disastrous effects. Accordingly, effectively sealing between the cartridge body and the inner surface of the barrel will avoid this possible problem.

While a full and complete description of the invention has been set forth in accordance with the dictates of the Patent Statutes, it should be understood that modifications thereof can be resorted to without departing from the spirit hereof or the scope of the appended claims.

What is claimed is:

1. In combination with a hypodermic syringe of the type having an elongate hollow body with a double-ended needle disposed on one end, a movable plunger on the opposed end, and aspirating means disposed adjacent the end carrying the needle, the improvement comprising;
   A. a cartridge having
      1. an elongate hollow body with a substantially uniform diameter throughout its length and having
         a. opposed first and second ends and
         b. being receivable within said body of said syringe, with said first end of said cartridge body being disposed adjacent said needle and said aspirating means and said second end being disposed adjacent said plunger;
   B. a first unitary resilient seal member
      1. received on said first end of said cartridge body in sealing relationship thereto and
      2. engaging the inner surface of said syringe body in sealing relationship therewith;
   C. a second unitary resilient seal member
      1. received on said second end of said cartridge body in sealing relationship thereto and
      2. engaging the inner surface of said cartridge body in sealing relationship therewith;
   D. said second seal member having
      1. a main body portion receivable within said second end of said cartridge body; and
      2. an annular flange on one end thereof normally adapted to engage and overlie the second end of said cartridge body and simultaneously engage the inner surface of said syringe body.

2. The cartridge of claim 1 wherein said main body portion has at least one projecting circumferential rib thereon.

3. The cartridge of claim 1 wherein the remaining end of said main body portion has an axially disposed blind opening therein which communicates with an enlarged cavity thereby forming a deformable projection.

4. The cartridge of claim 1 wherein said annular flange has an annular rib thereon.

* * * * *